(12) United States Patent
Brousmiche et al.

(10) Patent No.: US 10,258,979 B2
(45) Date of Patent: Apr. 16, 2019

(54) POROUS MATERIALS FOR SOLID PHASE EXTRACTION AND CHROMATOGRAPHY AND PROCESSES FOR PREPARATION AND USE THEREOF

(75) Inventors: Darryl W. Brousmiche, Grafton, MA (US); Kevin D. Wyndham, Upton, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 0 days.

(21) Appl. No.: 14/114,440

(22) PCT Filed: May 18, 2012

(86) PCT No.: PCT/US2012/038501
§ 371 (c)(1),
(2), (4) Date: Dec. 12, 2013

(87) PCT Pub. No.: WO2013/002909
PCT Pub. Date: Jan. 3, 2013

(65) Prior Publication Data
US 2014/0096596 A1    Apr. 10, 2014

Related U.S. Application Data

(60) Provisional application No. 61/488,561, filed on May 20, 2011.

(51) Int. Cl.
*B01J 20/285*    (2006.01)
*B01J 20/26*    (2006.01)
(Continued)

(52) U.S. Cl.
CPC .............. *B01J 43/00* (2013.01); *B01D 15/08* (2013.01); *B01J 20/264* (2013.01); *B01J 20/285* (2013.01);
(Continued)

(58) Field of Classification Search
CPC ........... C08F 226/06; C08J 2205/04–2205/046
See application file for complete search history.

(56) References Cited

U.S. PATENT DOCUMENTS 3,663,263 A      5/1972   Bodre et al.
5,334,310 A *    8/1994   Frechet et al. ............. 210/198.2
(Continued)

FOREIGN PATENT DOCUMENTS

EP         1159995 A2      5/2001
JP       2008185530 A     11/1999
(Continued)

OTHER PUBLICATIONS

Definition of copolymer. http://www.thefreedictionary.com/copolymer. As viewed on Nov. 9, 2016.*
(Continued)

*Primary Examiner* — Stephen E Rieth

(57) ABSTRACT

The invention provides novel porous materials that are useful in chromatographic processes, e.g., solid phase extraction, and that provide a number of advantages. Such advantages include superior wetting characteristics, selective capture of analytes of interest, and non-retention of interfering analytes. In certain aspects, the materials feature at least one hydrophobic component, at least one hydrophilic component and a average pore diameter of about 100 Å to about 1000 Å. In certain embodiments the materials also exhibit a nitrogen content from about 1% N to about 20% N. In certain embodiments, the materials also exhibit more than 10% of the BJH surface area of the porous material is contributed by pores that have a diameter greater than or equal to 200 Å. The invention advantageously provides novel porous materials having a large percentage of larger
(Continued)

pores (i.e. wide pores). The invention advantageously provides novel porous materials that overcome the problems of SPE of biological samples.

31 Claims, 10 Drawing Sheets

(51) Int. Cl.
    *B01D 15/08*     (2006.01)
    *B01J 43/00*     (2006.01)
    *B01J 20/28*     (2006.01)
    *B01J 39/20*     (2006.01)
    *B01J 41/14*     (2006.01)
    *G01N 1/40*     (2006.01)

(52) U.S. Cl.
    CPC ... *B01J 20/28057* (2013.01); *B01J 20/28078* (2013.01); *B01J 39/20* (2013.01); *B01J 41/14* (2013.01); *B01J 2220/82* (2013.01); *G01N 1/405* (2013.01)

(56) References Cited

U.S. PATENT DOCUMENTS

| | | | |
|---|---|---|---|
| 5,882,521 A * | 3/1999 | Bouvier et al. | 210/635 |
| 6,114,466 A | 9/2000 | Davankov et al. | |
| 6,156,851 A | 12/2000 | Davankov et al. | |
| 6,322,695 B1 * | 11/2001 | Lee et al. | 210/198.2 |
| 7,250,214 B2 | 7/2007 | Walter et al. | |
| 7,304,017 B2 * | 12/2007 | Leistner et al. | 502/402 |
| 7,442,299 B2 * | 10/2008 | Lee et al. | 210/198.2 |
| 7,731,844 B2 * | 6/2010 | Mallet et al. | 210/198.2 |
| 8,574,433 B2 * | 11/2013 | Lee et al. | 210/198.2 |
| 2002/0146413 A1 * | 10/2002 | Brady | A01N 1/0278 424/140.1 |
| 2002/0197252 A1 | 12/2002 | Brady et al. | |
| 2005/0032922 A1 | 2/2005 | Deorkar et al. | |
| 2006/0021939 A1 | 2/2006 | Mallet et al. | |
| 2006/0052559 A1 | 3/2006 | Gomez et al. | |
| 2010/0047904 A1 | 2/2010 | Forde et al. | |
| 2010/0076103 A1 * | 3/2010 | Wyndham | B01J 20/262 521/154 |
| 2012/0152847 A1 * | 6/2012 | Falkenhagen | B01D 15/00 210/691 |

FOREIGN PATENT DOCUMENTS

| | | | |
|---|---|---|---|
| JP | H11302304 A | | 11/1999 |
| JP | 2000514704 A | * | 11/2000 |
| JP | 2001343378 A | | 12/2001 |
| JP | 2001524878 A | * | 12/2001 |
| JP | 2002517574 A | * | 6/2002 |
| JP | 2004507594 A | | 3/2004 |
| JP | 2004-538468 A | | 12/2004 |
| JP | 2005514127 A | | 5/2005 |
| JP | 2006-68597 A | | 3/2006 |
| JP | 2006509066 A | | 3/2006 |
| JP | 2009-25315 A | | 2/2009 |
| JP | 2009-215566 A | | 9/2009 |
| JP | 2010515804 A | | 5/2010 |
| WO | 1993/07945 A1 | | 4/1993 |
| WO | WO-2003022392 A1 | | 3/2003 |
| WO | WO 2010083545 A2 * | 7/2010 | B01D 15/00 |

OTHER PUBLICATIONS

Lough, W. J.; Wainer, I. W. High Performance Liquid Chromatography Fundamental Principles and Practice. 1996. Chapman & Hall. pp. 66-67.*
Nawrocki, J. The silanol group and its role in liquid chromatography. Journal of Chromatography A, 1997, vol. 779, pp. 29-71.*
Wirth, H. J.; Gooley, A. Effects of particle porosity on the separation of larger molecules. SGE Analytical Science. Jun. 2009.*
Precision Measurement of the Specific Surface Area of Solids by Gas Adsorption. BAM Federal Institute for Materials Research and Testing. Jan. 2011.
Extended European Search Report, issued in corresponding European Patent Application No. EP 12804908.7, dated Jun. 9, 2015.
Extended European Search Report, issued in corresponding European Patent Application No. EP 12804908.7, dated Jun. 30, 2017.

* cited by examiner

3A)

3B)

3C)

Representative SEM of particles produced by the Process of Example 5.

Close-up SEM comparison of surface morphologies between wide pore particles of the invention and standard particles comprising non-polar porogens and N-vinylpyrrolidone.

Wide pore material | Standard material

Representative SEM of particles produced by the process of Example 6.

6A) Plot of Cumulative BJH Surface area ($m^2/g$) *vs.* Pore Diameter (Å) for representative materials of the invention *vs* standard material.

6B) Plot of Cumulative BJH Surface area (m²/g) vs. Pore Diameter (Å) for a representative material of the invention vs standard material.

6C) Plot of BJH Surface area (m$^2$/g) vs. Pore Diameter (Å) for representative materials of the invention vs standard material. Each point represents the BJH surface area contributed by the range (APD +50 Å) − APD.

6D) Condensed View - Plot of BJH Surface area (m²/g) vs. Pore Diameter (Å) for a representative material of the invention vs standard material. Each point represents the BJH surface area contributed by the range (APD +50 Å) – APD.

6E) Condensed View - Plot of BJH Surface area ($m^2/g$) vs. Pore Diameter (Å) for a representative material of the invention vs standard material. Each point represents the BJH surface area contributed by the range (APD +50 Å) – APD.

POROUS MATERIALS FOR SOLID PHASE EXTRACTION AND CHROMATOGRAPHY AND PROCESSES FOR PREPARATION AND USE THEREOF

RELATED APPLICATIONS

This application is a 371 U.S. National Phase Application of PCT/US2012/038501, filed May 18, 2012, which claims the benefit of U.S. provisional patent Ser. No. 61/488,561, filed May 20, 2011, the entire disclosures of which are incorporated herein by reference.

BACKGROUND OF THE INVENTION

Solid phase extraction (SPE) is a chromatographic technique that is widely used, e.g., for preconcentration and cleanup of analytical samples, for purification of various chemicals, and for removal of toxic or valuable substances from aqueous solutions. SPE is usually performed using a column or cartridge containing an appropriate material or sorbent. SPE procedures have been developed using sorbents that can interact with analytes by hydrophobic, ion-exchange, chelation, sorption, and other mechanisms, to bind and remove the analytes from fluids.

Because different SPE applications can require different sorbents, there is a need for sorbents with novel properties that have unique selectivities. These include superior wetting characteristics, selective capture of analytes of interest, and non-retention of interfering analytes. Sorbents comprising porous particles having the aforementioned properties are described in WO 99/64480 and in U.S. Pat. No. 6,322,695B 1.

The most common materials currently used are a copolymer of divinylbenzene and N-vinylpyrrolidinone with an average pore diameter of 73-89 Å. The pore size of this material is however too restrictive for samples of biological materials.

There remains a need for SPE materials with larger average pore diameters which maintain nitrogen content in the materials as well as particle morphology.

SUMMARY OF THE INVENTION

The invention provides novel porous materials that are useful in chromatographic processes, e.g., solid phase extraction, and that provide a number of advantages. Such advantages include superior wetting characteristics, selective capture of analytes of interest, and non-retention of interfering analytes. The invention advantageously provides novel porous materials having a large percentage of larger pores (i.e. wide pores). The invention advantageously provides novel porous materials that overcome the problems of SPE of biological samples.

In one aspect, the invention provides a porous material comprising a copolymer of a least one hydrophobic monomer and at least one hydrophilic monomer, wherein more than 10% of the Barret-Joyner-Halenda (BJH) surface area of the porous material is contributed by pores that have a diameter greater than or equal to 200 Å. In certain aspects, the BJH surface area and pore diameter are determined using a nitrogen gas adsorption desorption isotherm at 77.3K.

In another aspect, the invention provides a porous material comprising a copolymer of at least one hydrophobic monomer and at least one hydrophilic monomer, wherein said material has a median pore diameter of about 100Å to about 1000 Å.

In yet another aspect, the invention provides a porous material comprising a copolymer of at least one hydrophobic monomer and at least one hydrophilic monomer, wherein at least one of the hydrophilic monomers is a monomer having the formula:

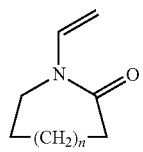

wherein n is an integer from 1-3.

In certain embodiments, the porous material of the invention comprises a porous particle that comprises said copolymer.

In certain other embodiments, the porous material of the invention comprises a porous monolith that comprises said copolymer.

In other embodiments, the porous material of the invention, said hydrophobic monomer is divinylbenzene or styrene.

In yet other embodiments, said hydrophobic monomer of the porous material of the invention is further substituted by at least one haloalkyl group.

In still other embodiments, said hydrophilic monomer of the porous material of the invention is N-vinylcaprolactam.

In other embodiments, said hydrophilic monomer of the porous material of the invention is not N-vinylpyrrolidone.

In yet other embodiments, said hydrophobic monomer of the porous material of the invention is further substituted by at least one haloalkyl group.

In still other embodiments, said hydrophilic monomer of the porous material of the invention is further substituted by at least one haloalkyl group.

In still other embodiments, said copolymer of the porous material of the invention is a poly(divinylbenzene-co-N-vinylcaprolactam).

In another aspect, the invention also provides solid phase extraction and chromatography materials comprising porous materials of the invention.

In yet another aspect, the invention provides a separation device comprising a porous material of the invention. In a related aspect, the invention provides a solid phase extraction cartridge comprising a porous material according to the invention.

The invention also provides a method for removing or isolating a component from a mixture. The method comprises contacting the mixture with a chromatographic material comprising the porous material according to the invention, to thereby remove or isolate the component from the mixture.

In another aspect, the invention provides a method for determining the level of a component in a mixture. The method comprises contacting the mixture with a chromatographic material comprising a porous material according to the invention under conditions that allow for sorption of the component onto the porous material; washing the chromatographic material having the sorbed component with a solvent under conditions so as to desorb the component from the porous materials; and determining the level of the desorbed component.

BRIEF DESCRIPTION OF THE DRAWINGS

FIGS. 6A-B show graphs of the cumulative BJH surface area vs the pore diameter. FIGS. 6C-E show graphs of the BJH surface area vs the pore diameter in which the value of the cumulative BJH surface area at the higher pore diameter is subtracted from the value at the next lowest pore diameter.

DETAILED DESCRIPTION OF THE INVENTION

Definitions

Figure 1:
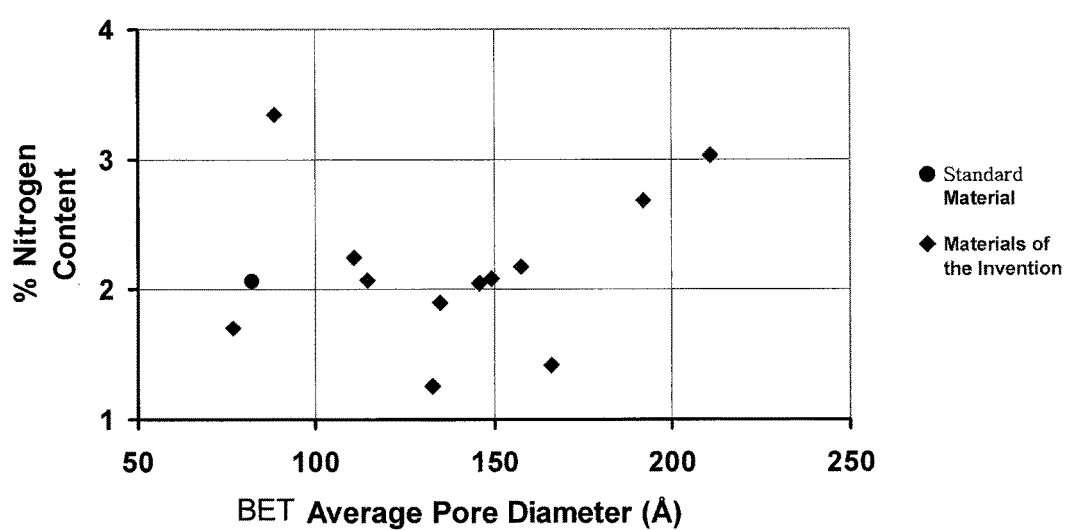
FIG. 1 depicts the percent nitrogen content vs. BET average pore diameter of representative porous materials of the invention and standard materials.
Figure 2:
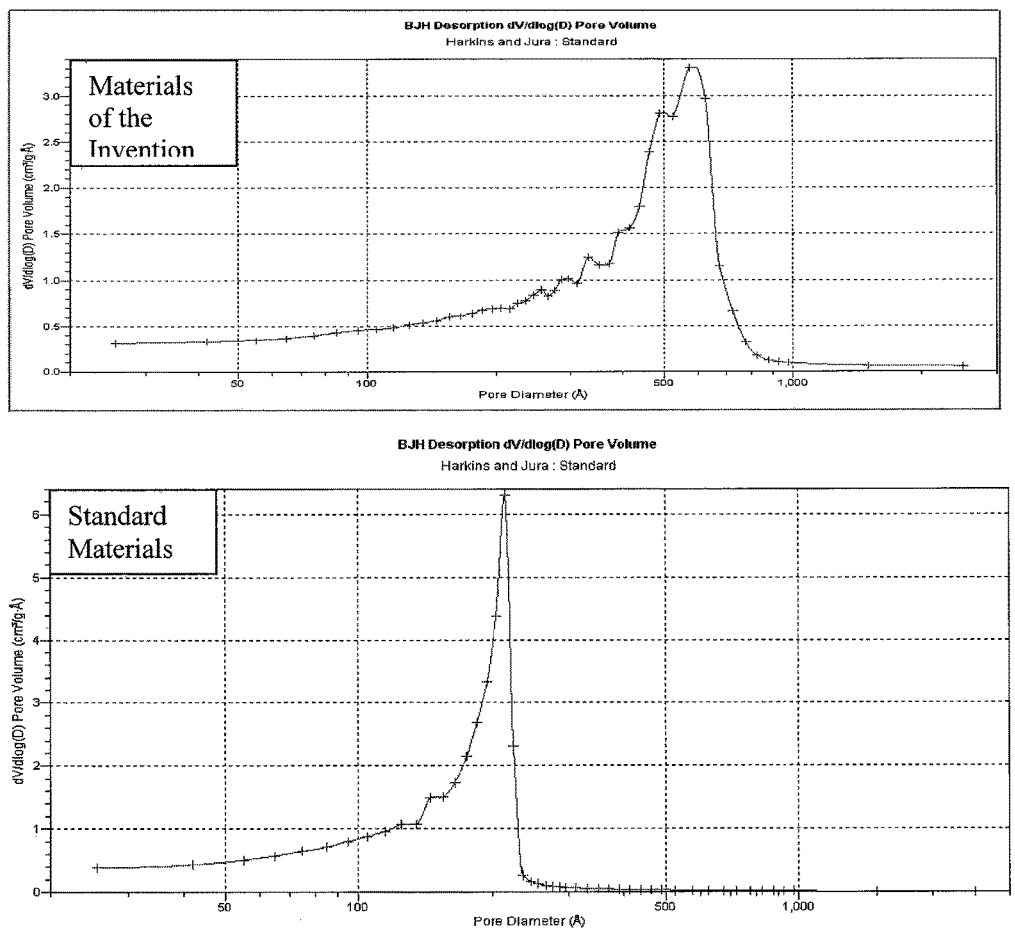
FIG. 2 depicts the BJH Desorption dV/dlog(D) pore volume plots of representative porous materials of the invention and standard materials. The graph presents pore diameter distributions of materials made by standard methods and those made by the methods of the invention as determined by BJH analysis
Figure 3:
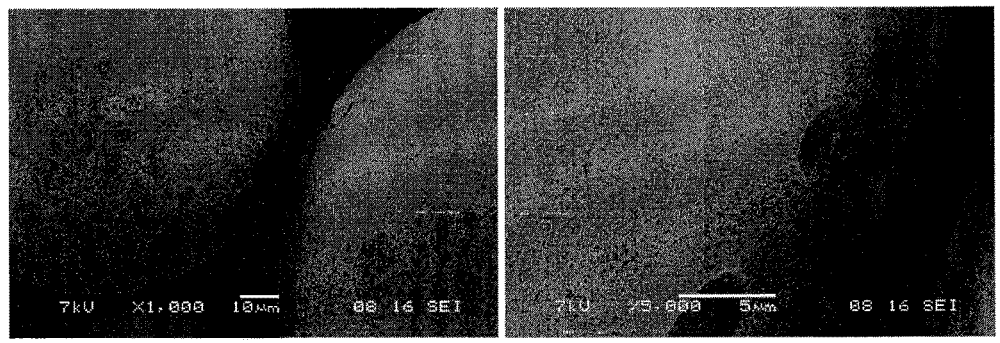
FIG. 3 shows SEM depictions of a) standard materials having a BET average pore diameter of about 91 Å; b) materials of the invention having a BET average pore diameter of about 146 Å. and c) materials of the invention having an average pore diameter of about 500 Å.
Figure 3:
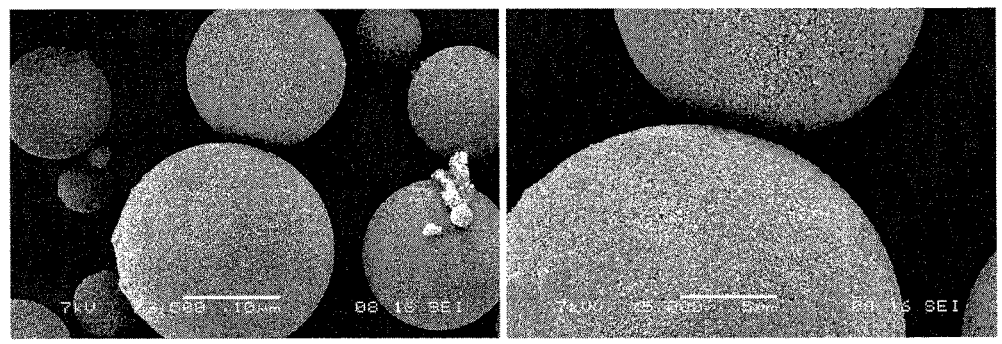
Figure 3:
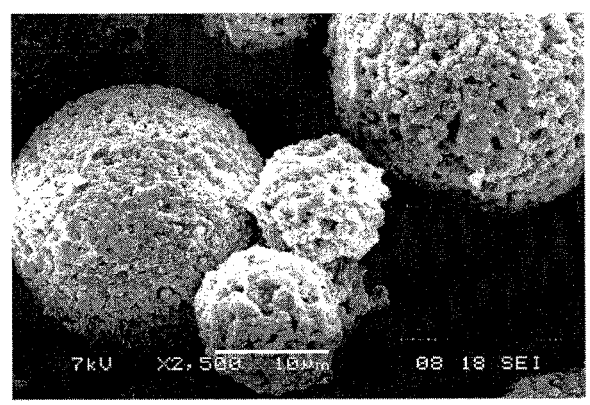

The present invention will be more fully illustrated by reference to the definitions set forth below.

The term "BET surface area" describes the specific surface area of a material as determined by standard BET techniques for analysis of gas adsorption-desorption, such as those described in Gregg, S. J. and Sing, K. S. W. (1982) Adsorption, Surface Area and Porosity, p. 303 Academic Press, London; and Lowell, S. and Shields, J. E. (1991) Powder surface area and porosity (3rd edition), p. 245. Chapman and Hall, U.K. In specific aspects of the invention, the BET surface area is as measured by BET analysis of nitrogen gas adsorption at 77.3K.

The term "BJH surface area" describes the specific surface area of a material as determined by standard BJH techniques for analysis, such as those described in Barret et al. *J. Am. Chem. Soc.* (1951), vol. 73, pp. 373-380 In specific aspects of the invention, the BJH surface area and pore diameter are determined using a nitrogen gas adsorption desorption isotherm at 77.3K.

The term "hydrophilic" describes having an affinity for, attracting, adsorbing or absorbing water.

The term "hydrophobic" describes lacking an affinity for, repelling, or failing to adsorb or absorb water.

The term "ion-exchange functional group" is intended to include a group where the counter-ion is partially free and can readily be exchanged for other ions of the same sign.

The term "mole percent" describes the mole fraction, expressed as a percent, of the monomer of interest relative to the total moles of the various (two or more) monomers that comprise the copolymer of the porous material of the invention.

The term "monolith" is intended to include a porous, three-dimensional material having a continuous interconnected pore structure in a single piece. A monolith is prepared, for example, by casting precursors into a mold of a desired shape. The term monolith is meant to be distinguished from a collection of individual particles packed into a bed formation, in which the end product still comprises individual particles in bed formation.

The term "monomer" is intended to include a molecule comprising one or more polymerizable functional groups prior to polymerization, or a repeating unit of a polymer.

The term "porous material" is intended to include a member of a class of porous crosslinked polymers penetrated by pores through which solutions can diffuse. Pores are regions between densely packed polymer chains.

The term "random ordering" is intended to include ordering in which individual units are joined randomly.

The term "solid phase extraction" is intended to include a process employing a solid phase for isolating classes of molecular species from fluid phases such as gases and liquids by, e.g., sorption, ion-exchange, chelation, size exclusion (molecular filtration), affinity or ion pairing mechanisms.

The term "sorption" describes the ability of a material to take up and hold another material by absorption or adsorption.

The term "surface modifiers" includes (typically) functional groups which impart a certain chromatographic functionality to the material.

The language "surface modified" is used herein to describe the composite material of the present invention that possess organic groups which may additionally be substituted or derivatized with a surface modifier. "Surface modifiers" include (typically) organic functional groups that impart a certain chromatographic functionality to the material.

The language "surface functionalized" is used herein to describe the composite material of the present invention that possess ion-exchange functional groups that impart a certain chromatographic functionality to the material.

BET and BJH Analysis

BET theory is used to explain the physical adsorption of gas molecules on a solid surface. The theory was developed by Stephen Brunauer, Paul Hugh Emmett, and Edward Teller and serves as the basis for an important analysis technique for the measurement of the specific surface area of a material.

In physical gas adsorption, an inert gas, typically nitrogen, is adsorbed on the surface of a solid material. This occurs on the outer surface and, in case of porous materials, also on the surface of pores. Adsorption of nitrogen at a temperature of 77 K leads to a so-called adsorption isotherm, sometimes referred to as BET isotherm, which is mostly measured over porous materials. In specific cases, the use of argon adsorption, carbon dioxide or krypton gas adsorption may be used instead of nitrogen adsorption to accurately probe the micropores.

Monolayer formation of gas molecules on the surface is used to determine the specific surface area, while the principle of capillary condensation can be applied to assess the presence of pores, pore volume and pore size distribution.

In general, two different techniques can be distinguished:

The flow technique uses a detector to obtain information on the amount of adsorbed gas resulting in a specific BET surface area and/or total pore volume.

The volumetric technique measures many adsorption and/or desorption points providing a full isotherm with information on BET surface area, pore volume and pore size distribution.

Standard BET analysis techniques are well known in the art and can be found, for example, in Gregg, S. J. and Sing, K. S. W. (1982) Adsorption, Surface Area and Porosity, p. 303 Academic Press, London and in Lowell, S. and Shields, J. E. (1991) Powder surface area and porosity (3rd edition), p. 245. Chapman and Hall, U.K. The disclosures of each of these references are incorporated herein by reference in their entireties.

BJH Analysis is used to estimate the volume and area of porous adsorbents available to molecules of various sizes. BJH Analysis is related to the BET and can also be employed to determine pore area and specific pore volume using adsorption and desorption techniques. This technique characterizes pore size distribution independent of external area due to particle size of the sample. BJH Analysis was developed by Elliot Barrett, Leslie Joyner and Paul Halenda.

Figure 6:
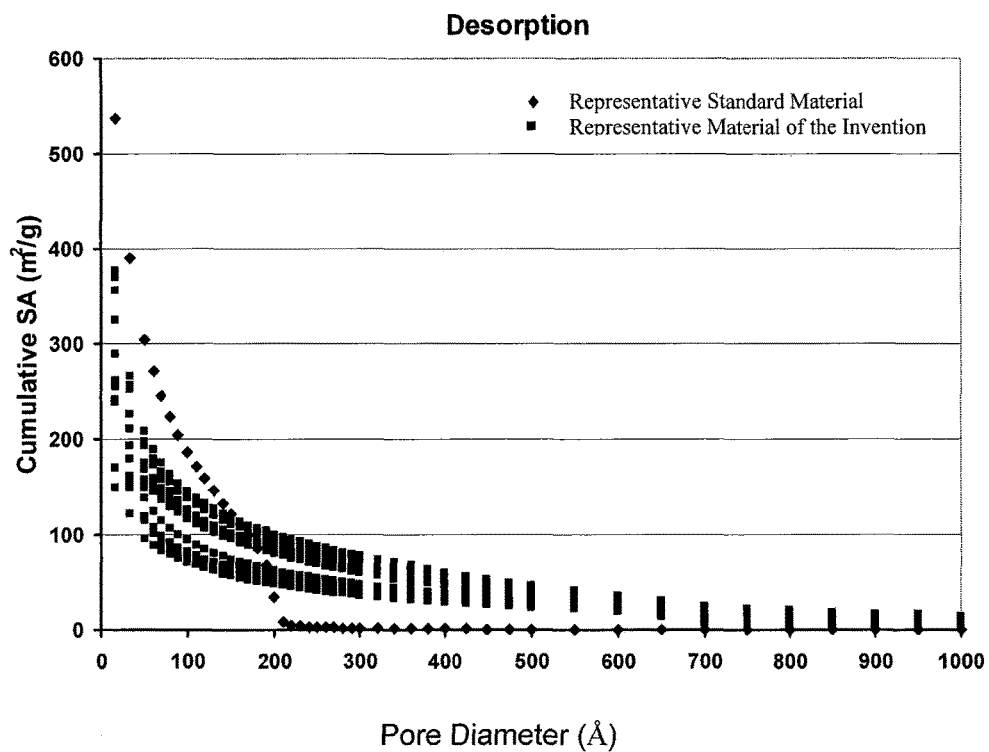
FIG. 6 shows representative plots of the BJH surface area vs pore diameter of representative compounds of the invention as compared to a standard material as determined using a nitrogen gas desorption isotherm at 77.3K.
Figure 6:
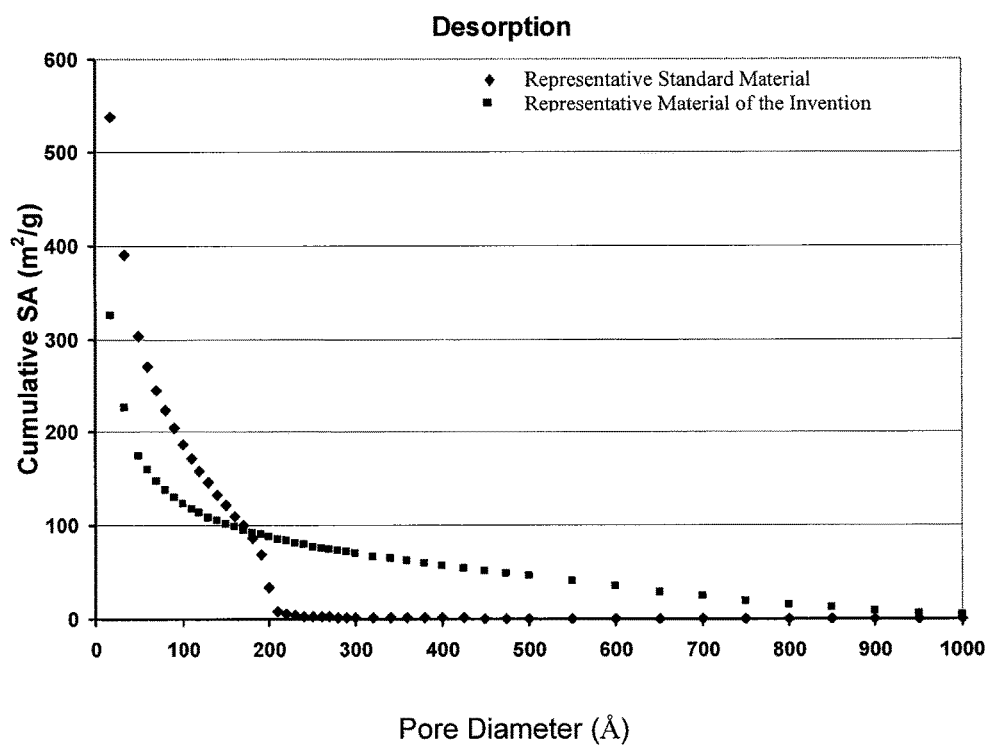
Figure 6:
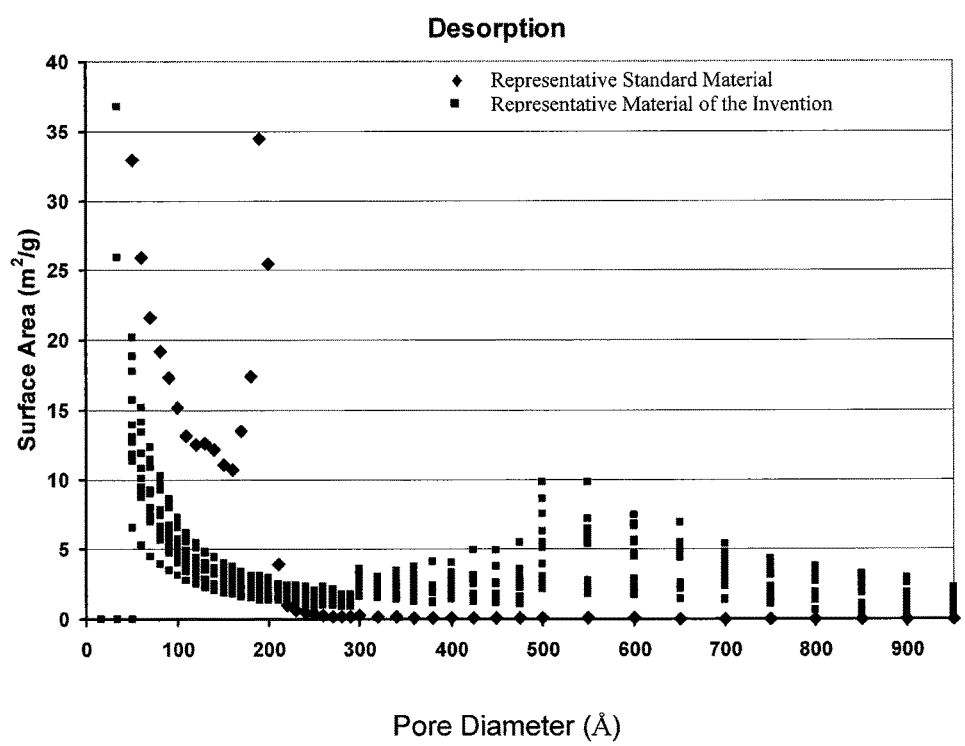
Figure 6:
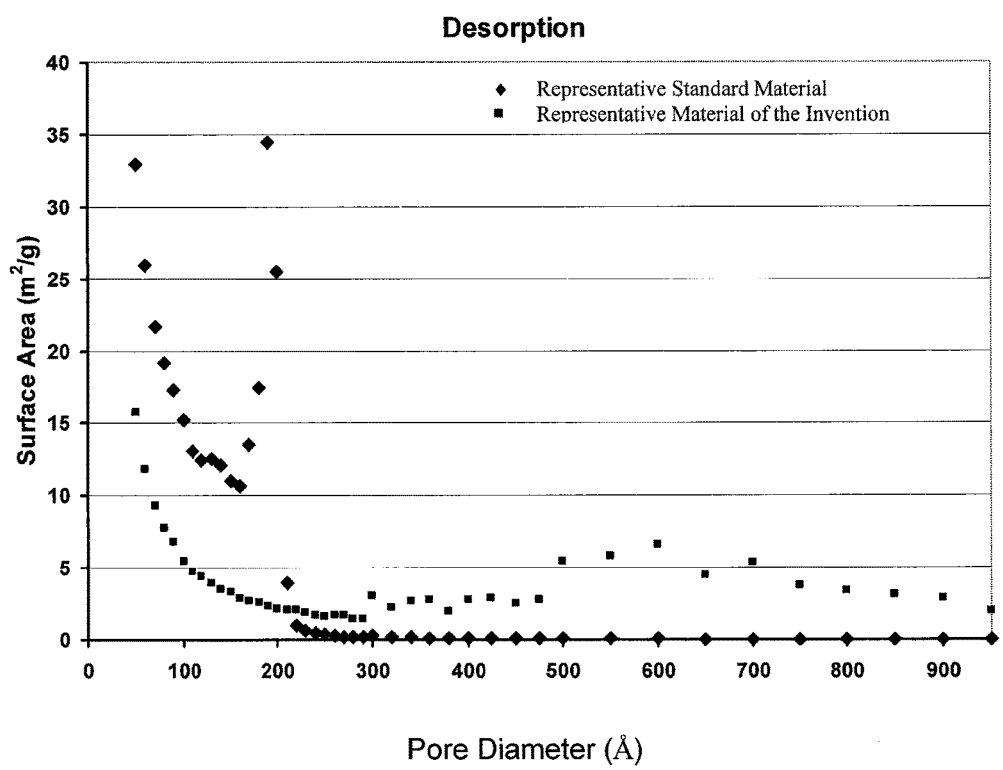
Figure 6:
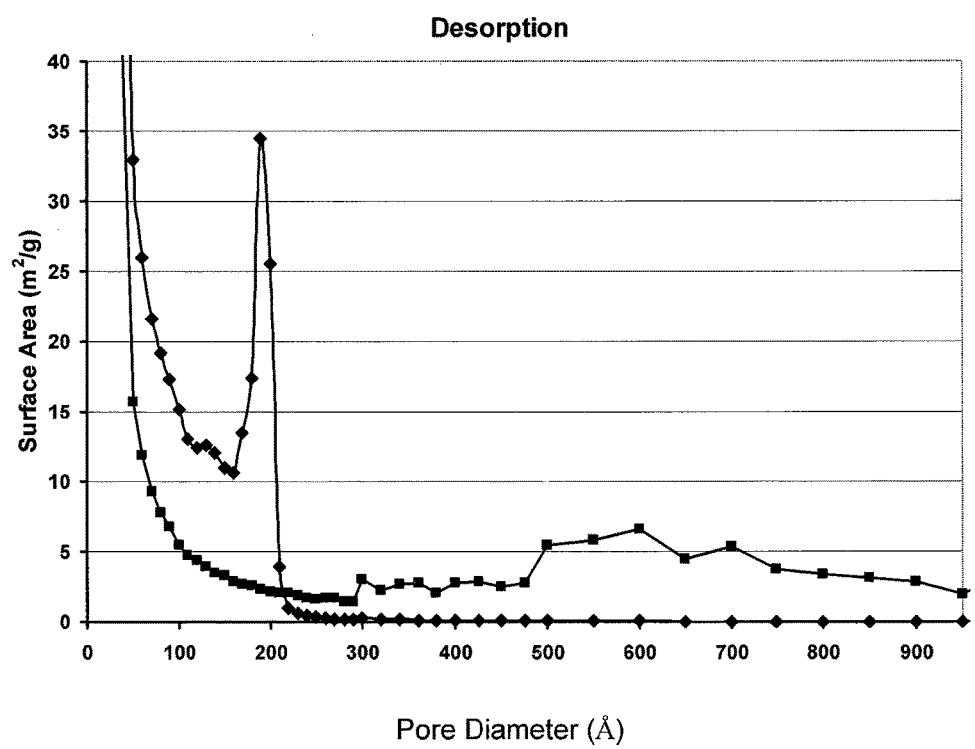

FIG. 6 shows representative plots of the BJH surface area vs pore diameter of representative compounds of the invention as compared to a standard material as determined using a nitrogen gas desorption isotherm at 77.3K. FIGS. 6A-B show graphs of the cumulative BJH surface area vs the pore diameter. FIGS. 6C-E show graphs of the BJH surface area vs the pore diameter in which the value of the cumulative BJH surface area at the higher pore diameter is subtracted from the value at the next lowest pore diameter. Thus, the associated BJH surface area in FIGS. 6C-E is not a cumulative surface area, but rather, a representation of the overall surface area associated with or contributed by a given pore diameter across the range of the subtraction. Thus, for example, the value shown at 900 in the FIG. 6C-E graphs is representative of the BJH surface area associated with the 900 to 950 Å pores.

The percentage of the BJH surface area contributed by pores greater than 200 Å, for example, can be calculated by dividing the cumulative BJH surface from 200 Å to 2000 Å by the cumulative BJH surface area from the lowest pore diameter recorded (e.g. 17 Å) to 2000 Å—which represents the total BET surface area of the material—and multiplying by 100.

Compositions and Methods of the Invention

In one aspect, the invention provides a porous material comprising a copolymer of a least one hydrophobic monomer and at least one hydrophilic monomer, wherein more than 10% of the BJH surface area of the porous material is contributed by pores that have a diameter greater than or equal to 200 Å. In certain aspects, more than 12.5% of the BJH surface area of the porous material is contributed by pores that have a diameter greater than or equal to 200 Å. In other aspects, more than 15% of the BJH surface area of the porous material is contributed by pores that have a diameter greater than or equal to 200 Å . In yet other aspects, more than 17.5% of the BJH surface area of the porous material is contributed by pores that have a diameter greater than or equal to 200 Å.

In another aspect, the invention provides a porous material comprising a copolymer of a least one hydrophobic monomer and at least one hydrophilic monomer, wherein more than 10% of the BJH surface area of the porous material is contributed by pores that have a diameter greater than or equal to 300 Å. In certain aspects, more than 12.5% of the BJH surface area of the porous material is contributed by pores that have a diameter greater than or equal to 300 Å. In other aspects, more than 15% of the BJH surface area of the porous material is contributed by pores that have a diameter greater than or equal to 300 Å.

In still another aspect, the invention provides a porous material comprising a copolymer of a least one hydrophobic monomer and at least one hydrophilic monomer, wherein more than 12.5% of the BJH surface area of the porous material is contributed by pores that have a diameter greater than or equal to 200 Å and more than 10% of the BJH surface area of the porous material is contributed by pores that have a diameter greater than or equal to 300 Å. In certain embodiments, more than 15% of the BJH surface area of the porous material is contributed by pores that have a diameter greater than or equal to 200 Å and more than 10% of the BJH surface area of the porous material is contributed by pores that have a diameter greater than or equal to 300 Å. In other embodiments, more than 17.5% of the BJH surface area of the porous material is contributed by pores that have a diameter greater than or equal to 200 Å and more than 10% of the BJH surface area of the porous material is contributed by pores that have a diameter greater than or equal to 300 Å.

In yet another aspect, the invention provides a porous material comprising a copolymer of a least one hydrophobic monomer and at least one hydrophilic monomer, wherein, more than 15% of the BJH surface area of the porous material is contributed by pores that have a diameter greater than or equal to 200 Å and more than 12.5% of the BJH surface area of the porous material is contributed by pores that have a diameter greater than or equal to 300 Å. In other embodiments, more than 17.5% of the BJH surface area of the porous material is contributed by pores that have a diameter greater than or equal to 200 Å and more than 12.5% of the BJH surface area of the porous material is contributed by pores that have a diameter greater than or equal to 300 Å.

In still yet another aspect, the invention provides a porous material comprising a copolymer of a least one hydrophobic monomer and at least one hydrophilic monomer, wherein more than 17.5% of the BJH surface area of the porous material is contributed by pores that have a diameter greater than or equal to 200 Å and more than 15% of the BJH surface area of the porous material is contributed by pores that have a diameter greater than or equal to 300 Å.

In yet another aspect, the BJH surface area of the porous materials of the invention as described herein is measured by BJH analysis of nitrogen gas adsorption at 77.3K.

In another aspect, the invention provides a porous material comprising a copolymer of a least one hydrophobic monomer and at least one hydrophilic monomer, wherein said material has a median pore diameter of about 100 Å to about 1000 Å. Median pore diameter can be measured, for example, by inverse size exclusion chromatography (I-SEC). In certain aspects, the material has a median pore diameter of about 200 Å to about 800 Å; about 300 Å to about 550 Å; about 100 Å; about 200 Å; about 300 Å; about 400 Å; about 425; about 450 Å; about 475 Å; about 500 Å; about 525 Å; about 550 Å; about 575 Å; about 600 Å; about 700 Å; or about 800 Å.

The invention further provides a porous material comprising a copolymer of a least one hydrophobic monomer and at least one hydrophilic monomer, wherein said material has nitrogen content from about 0.5% N to about 20% N; from about 1% N to about 10% N; from about 1% N to about 5% N; from about 1% N to about 4% N; about 1% N; about 1.5% N; about 2% N; about 2.5% N; about 3% N; about 3.5% N; about 4% N; about 4.5% N; about 5% N; about 5.5% N; about 6% N; about 6.5% N; about 7% N; about 7.5% N; about 8% N; about 8.5% N; about 9% N; about 9.5% N; about 10% N; about 10.5% N; about 11% N; about 11.5% N; about 12% N; about 12.5% N; about 13% N; about 13.5% N; about 14% N; about 14.5% N; or about 15% N In certain embodiments, the porous material of the invention has both a median pore diameter of about 100 Å to about 1000 Å; about 200 Å to about 900 Å; about 300 Å to about 800 Å; or about 300 Å to about 550 Å; and a nitrogen content from about 0.5% N to about 20% N; from about 1% N to about 10% N; from about 1% N to about 5% N; from about 1% N to about 4% N; about 1% N; about 1.5% N; about 2% N; about 2.5% N; about 3% N; about 3.5% N; about 4% N; about 4.5% N; about 5% N; about 5.5% N; about 6% N; about 6.5% N; about 7% N; about 7.5% N; about 8% N; about 8.5% N; about 9% N; about 9.5% N; about 10% N; about 10.5% N;

about 11% N; about 11.5% N; about 12% N; about 12.5% N; about 13% N; about 13.5% N; about 14% N; about 14.5% N; or about 15% N.

In other embodiments, the porous material comprising a copolymer of a least one hydrophobic monomer and at least one hydrophilic monomer, wherein said material has an oxygen content from about 1% O to about 20% O; from about 1% O to about 10% O; from about 1% O to about 5% O; from about 1% O to about 4% O; about 1% O; about 2% O; about 3% O; about 4% O; about 5% O; about 6% O; about 7% O; about 8% O; about 9% O; about 10% O; about 11% O; about 12% O; about 13% O; about 14% O; or about 15% O.

In yet other embodiments, the porous material comprising a copolymer of a least one hydrophobic monomer and at least one hydrophilic monomer, wherein said material has a sulfur content from about 1% S to about 20% S; from about 1% S to about 10% S; from about 1% S to about 5% S; from about 1% S to about 4% S; about 1% S; about 2% S; about 3% S; about 4% S; about 5% S; about 6% S; about 7% S; about 8% S; about 9% S; about 10% S; about 11% S; about 12% S; about 13% S; about 14% S; or about 15% S.

In still other embodiments, the porous material comprising a copolymer of a least one hydrophobic monomer and at least one hydrophilic monomer, wherein said material has a phosphorous content from about 1% P to about 20% P; from about 1% P to about 10% P; from about 1% P to about 5% P; from about 1% P to about 4% P; about 1% P; about 2% P; about 3% P; about 4% P; about 5% P; about 6% P; about 7% P; about 8% P; about 9% P; about 10% P; about 11% P; about 12% P; about 13% P; about 14% P; or about 15% P.

In certain aspects, the porous material has a specific surface area in the range from about 50 to about 850 square meters per gram and pores having a diameter ranging from about 50 Å to 1000 Å.

In certain embodiments, the porous materials of the invention take the form of porous particles, e.g., beads, pellets, or any other form desirable for use. The porous particles can have, e.g., a spherical shape, a regular shape or an irregular shape. In some embodiments, the particles are beads having a diameter in the range from about 3 to about 500 μm, from about 10 to about 300 μm, or from about 20 to about 200 μm. In other embodiments, the particles are beads having a diameter in the range from about 3 to about 30 μm, from about 5 to about 20 μm, or from about 10 to about 15 μm.

In other embodiments, the porous materials of the invention take the form of porous monoliths. In certain embodiments, the monoliths have the following characteristics: surface area ranging from about 50 to about 800 m²/g, more particularly about 300 to about 700 m²/g; pore volume ranging from about 0.2 to about 2.5 cm³/g, more particularly about 0.4 to about 2.0 cm³/g, still more particularly about 0.6 to about 1.4 cm³/g; and pore diameter ranging from about 20 to about 500 Å, more particularly about 50 to about 300 Å, still more particularly about 80 to about 150 Å.

Component Materials of the Invention

The porous materials of the invention comprise a copolymer comprising a least one hydrophobic monomer and at least one hydrophilic monomer. In certain embodiments, the copolymer of the invention is non-sulfonated. In certain other embodiments, the copolymer is sulfonated.

Hydrophobic Monomers

In certain embodiments the hydrophobic monomer comprises an aromatic carbocyclic group, e.g., a phenyl group or a phenylene group, or a straight chain $C_2$-$C_{18}$-alkyl group or a branched chain $C_2$-$C_{18}$-alkyl group. The hydrophobic monomer can be, e.g., styrene or divinylbenzene. A preferred copolymer is a poly(divinylbenzene-co-N-vinylcaprolactam).

In one embodiment, the hydrophobic monomer is divinylbenzene or styrene, and the hydrophilic monomer is N-vinylcaprolactam or N-vinyl acetamide. In a specific embodiment, the copolymer is a poly(divinylbenzene-co-N-vinylcaprolactam). In certain embodiments, the porous material comprises at least about 8 mole percent N-vinylcaprolactam. In still other embodiments, the porous material comprises at least about 15 mole percent N-vinylcaprolactam. In yet other embodiments, the porous material comprises from about 5 to about 35 mole percent N-vinylcaprolactam; from about 7 to about 33 mole percent N-vinylcaprolactam; from about 9 to about 32 mole percent N-vinylcaprolactam; from about 10 to about 30 mole percent N-vinylcaprolactam; from about 15 to about 30 mole percent N-vinylcaprolactam; from about 17.3 to about 29.6 mole percent N-vinylcaprolactam.

In some embodiments, the hydrophobic monomer is further substituted by at least one haloalkyl group.

Hydrophilic Monomers

In certain embodiments the hydrophilic monomer is a monomer having the formula:

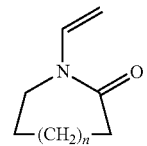

Wherein n is an integer from 1-3.

In certain other embodiments, the hydrophilic monomer is N-vinylcaprolactam. In specific embodiments, the hydrophilic monomer is not N-vinylpyrrolidone.

In some embodiments, the hydrophilic monomer is further substituted by at least one haloalkyl group.

In certain embodiments the hydrophilic monomer comprises one or more sulfur, phosphorous, nitrogen and/or oxygen atoms.

The porous materials, in either porous particle or monolith form, are advantageously used for solid phase extraction or chromatography. In a one embodiment, the porous material comprises at least one porous particle, and more preferably a plurality of porous particles. In one embodiment, the porous material comprises the copolymer poly(divinylbenzene-co-N-vinylcaprolactam). In a related embodiment, the poly(divinylbenzene-co-N-vinylcaprolactam) has ion-exchange functional moieties present at a concentration of about 0.01 to about 10.0 milliequivalents per gram of porous material; about 0.01 to about 5.0 milliequivalents per gram of porous material; about 0.01 to about 3.0 milliequivalents per gram of porous material; or about 0.01 to about 1.0 milliequivalents per gram of porous material.

Surface Functionalization/Modification

The porous materials, in either porous particle or monolith form, may be functionalized to provide an ion-exchange functional moiety.

In certain embodiments, the ion-exchange functional moiety can be formed by formation of an amine functionality on materials of the invention after cholomethylation as in the methods described in U.S. Pat. No. 7,731,844, which is incorporated herein by reference. In other embodiments, an amine functionality can be formed by direct reaction with a neat amine.

In accordance with the invention, the ion-exchange functional moiety can be formed from a substituted acyclic amine or a substituted cyclic amine. The substitution can be at any of the ring atoms, including heteroatoms. For example, in certain embodiments, the ion-exchange functional moiety is a substituted cyclic secondary amine, e.g., N-methyldiazinane and 4-methylpiperidine.

In other embodiments, the aforesaid amines are advantageously substituted by an electron withdrawing group. In certain embodiments, the electron withdrawing group is selected from the group consisting of halogens, aromatic groups, unsaturated groups, ethers, thioethers, nitriles, nitro groups, esters, amides, carbamates, ureas, carbonates, sulfonamides, sulfones, sulfoxides and heteroatoms, e.g., N, O and S. In certain embodiments, the electron withdrawing group is a halogen, an ether, or an aromatic group.

In accordance with the invention, the electron withdrawing group of the amine has the effect of lowering the average $pK_a$ of the conjugate acid of the amine as compared to the conjugate acid of the amine without the electron withdrawing group. In certain embodiments, the $pK_a$ ranges from about 5 to about 7.

In certain embodiments, the acyclic amine substituted with an electron withdrawing group includes benzylamine, N-methylbenzylamine, N-ethylbenzylamine, N-propylbenzylamine, N-butylbenzylamine, N-pentylbenzylamine, N-hexylbenzylamine, N-heptylbenzylamine, N-octylbenzylamine, N-nonylbenzylamine, N-decylbenzylamine, N-undecylbenzylamine, N-dodecylbenzylamine, N-tridecylbenzylamine, N-tetradecylbenzylamine, N-pentadecylbenzylamine, N-hexadecylbenzylamine, N-heptadecylbenzylamine, N-octadecylbenzylamine, dibenzylamine, aniline, N-methylaniline, N-ethylaniline, N-propylaniline, N-butylaniline, N-pentylaniline, N-hexylaniline, N-heptylaniline, N-octylaniline, N-nonylaniline, N-decylaniline, N-undecylaniline, N-dodecylaniline, N-tridecylaniline, N-tetradecylaniline, N-pentadecylaniline, N-hexadecylaniline, N-heptadecylaniline, N-octadecylaniline, bis(2,2,2-trifluoromethyl) amine, phenethylamine, N-methylphenethylamine, 4-methylphenethylamine, 3-phenylpropylamine, 1-methyl-3-phenylpropylamine, N-isopropylbenzylamine, and 4-phenylbutylamine. In certain preferred embodiments, the acyclic amine substituted with an electron withdrawing group is benzylamine, N-methylbenzylamine, or phenethylamine. In a preferred embodiment, the acyclic amine substituted with an electron withdrawing group is N-methylbenzylamine.

In other embodiments, cyclic secondary amines substituted with an electron withdrawing group include oxazetane, oxazolane, oxazinane, oxazepane, oxazocane, oxazonane, oxazecane, thiazetane, thiazolane, thiazinane, thiazepane, thiazocane, thiazonane, and thiazecane. In one embodiment, the cyclic secondary amine is 1,4-oxazinane. In these embodiments, one of ordinary skill in the art will appreciate that the electron withdrawing group is a second heteroatom that has substituted for a carbon atom in the ring. For example, the ring carbon adjacent to the nitrogen atom in azetidine is substituted by an oxygen to yield oxazetane, an amine encompassed by the term "cyclic secondary amine substituted with an electron withdrawing group".

In still other embodiments, an ion-exchange functional moiety can be formed by reaction of the materials of the invention with hydrogen peroxide.

In certain embodiments, surface functionalization can be attained on the materials of the invention by the methods described in U.S. Pat. No. 7,232,520 and U.S. Pat. No. 7,731,844, which are incorporated herein by reference.

In another embodiment, the materials of the invention may be surface modified by coating with a polymer.

In still another embodiment, the materials of the invention may be surface modified by a combination of organic group modification and coating with a polymer. In a further embodiment, the organic group comprises a chiral moiety.

In other embodiments, the materials of the invention may be surface modified via formation of an organic covalent bond between an organic group on the material and the modifying reagent.

Grafted Materials

In certain embodiments, the porous materials of the invention comprise a porous or non-porous core, including, but not limited to an inorganic core, an organic core or a hybrid core onto which a copolymer comprising a least one hydrophobic monomer and at least one hydrophilic monomer is grafted. In certain other embodiments, the porous materials of the invention comprise a polymeric, porous core made from at least one hydrophobic monomer onto which a polymer made from a least one hydrophilic monomer is grafted. In still other embodiments, the porous materials of the invention comprise a polymeric, porous core made from at least one hydrophilic monomer onto which a polymer made from a least one hydrophobic monomer is grafted.

In such embodiments, the hydrophilic and hydrophobic monomers may be as described herein. The cores may include a silica material; a hybrid inorganic/organic material; a superficially porous material; or a superficially porous particle.

Methods of Preparation

The porous materials of the invention can be prepared via a number of processes and mechanisms including, but not limited to, chain addition and step condensation processes, radical, anionic, cationic, ring-opening, group transfer, metathesis, and photochemical mechanisms.

The copolymer can be prepared via standard synthetic methods known to those skilled in the art, e.g., as described in the examples.

Furthermore, porous material may be produced by known methods, such as those methods described in, for example, in U.S. Pat. Nos. 4,017,528; 6,528,167; 6,686,035; 7,175,913; 7,731,844 and WO2004/041398.

Uses and Applications

The novel materials of the invention, e.g., in the form of porous particles or monoliths, can be used for solid phase extraction and chromatography. Thus, the invention also provides a porous material for solid phase extraction or chromatography comprising at least one ion-exchange functional group, at least one hydrophilic component and at least one hydrophobic component. The ion-exchange functional groups enable the porous material to interact with anionic, cationic, acidic and/or basic solutes. The hydrophilic polar components enable the porous material to have polar interactions and hydrogen bonding capabilities with solutes. The hydrophobic components enable the porous material to have affinity towards nonpolar solutes through hydrophobic interaction. Since the porous materials of this invention have a combination of various interaction forces towards solutes, they are very useful materials for, e.g., solid phase extraction, ion-exchange, and liquid chromatography applications. For example, these novel porous materials can be used to bind, recover and/or remove solutes from fluids. Similarly, these novel porous materials have certain chemical affinities or attractions between the materials and certain molecules, particularly biological or biochemical molecules, such as proteins, peptides, hormones, oligonucleotides, polynucleotides, vitamins, cofactors, metabolites, lipids and carbohydrates. As such, the materials of the invention may be used to selectively adsorb and isolate certain biomolecules for analysis and or quantification.

The invention also provides a method for removing or isolating a component, e.g., a solute, from a mixture. A solution having a solute is contacted with a porous material of the invention under conditions that allow for sorption of the solute to the porous material.

The solute can be, e.g., any molecule having a hydrophobic, hydrophilic, or ionic interaction or a combination of two or three of these interactions. Preferably, the solute is an organic compound of polarity suitable for adsorption onto the porous material. Such solutes include, e.g., drugs, pesticides, herbicides, toxins and environmental pollutants, e.g., resulting from the combustion of fossil fuels or other industrial activity, such as metal-organic compounds comprising a heavy metal such mercury, lead or cadmium. The solutes can also be metabolites or degradation products of the foregoing materials. Solutes also include, e.g., biomolecules, such as proteins, peptides, hormones, oligonucleotides, polynucleotides, vitamins, cofactors, metabolites, lipids and carbohydrates. Solutes also include, e.g., modified proteins, modified oligonucleotides, single-stranded oligonucleotides, double-stranded oligonucleotides, DNA, and RNA.

The solution e.g., can comprise water, an aqueous solution, or a mixture of water or an aqueous solution and a water-miscible polar organic solvent, e.g., methanol, ethanol, N,N-dimethylformamide, dimethylsulfoxide or acetonitrile. In a preferred embodiment, the solution is an acidic, basic or neutral aqueous, i.e., between about 0% and about 99% water by volume, solution. Specific examples are provided in the experimentals. The solution comprising the solute can, optionally, further contain one or more additional solutes. In one embodiment, the solution is an aqueous solution which includes a complex variety of solutes. Solutions of this type include, e.g., blood, plasma, urine, cerebrospinal fluid, synovial fluid and other biological fluids, including, e.g., extracts of tissues, such as liver tissue, muscle tissue, brain tissue or heart tissue. Such extracts can be, e.g., aqueous extracts or organic extracts which have been dried and subsequently reconstituted in water or in a water/organic mixture. Solutions also include, e.g., ground water, surface water, drinking water or an aqueous or organic extract of an environmental sample, such as a soil sample. Other examples of solutions include a food substance, such as a fruit or vegetable juice or milk or an aqueous or aqueous/organic extract of a food substance, such as fruit, vegetable, cereal or meat. Other solutions include, e.g., natural products extractions from plants and broths.

The solution can be contacted with the porous material in any fashion which allows sorption of the solute to the porous material, such as a batch or chromatographic process. For example, the solution can be forced through a porous polymer column, disk or plug, or the solution can be stirred with the porous material, such as in a batch-stirred reactor.

The solution can also be added to a porous material-containing well of a microtiter plate. The porous material can take the form of a monolith or particle, e.g., beads or pellets. The solution is contacted with the porous material for a time period sufficient for the solute of interest to substantially sorb onto the porous material. This period is typically the time necessary for the solute to equilibrate between the porous material surface and the solution. The sorption or partition of the solute onto the porous material can be partial or complete.

The invention also includes a method for analytically determining the level of solute in a solution. A solution having a solute is contacted with a porous material under conditions so as to allow sorption of the solute to the porous material. The material comprises at least one ion-exchange functional group, at least one hydrophilic polar component and at least one hydrophobic component. The porous material having the sorbed solute is washed with a solvent under conditions so as to desorb the solute from the porous material. The level of the desorbed solute present in the solvent after the washing is analytically determined.

The solution contacted with the porous material can comprise the solute of interest in dilute form, e.g., at a concentration too low for accurate quantitation. By sorbing the solute onto the porous material and then, e.g., desorbing the solute with a substantially smaller volume of a less polar solvent, a solution which includes the solute of interest can be prepared having a substantially higher concentration of the solute of interest than that of the original solution. The method can also result in solvent exchange, that is, the solute is removed from a first solvent and re-dissolved in a second solvent.

Solvents which are suitable for desorbing the solute from the porous material can be, e.g., polar water-miscible organic solvents, such as alcohols, e.g., methanol, ethanol or isopropanol, acetonitrile, acetone, and tetrahydrofuran, or mixtures of water and these solvents. The desorbing solvent can also be, e.g., a nonpolar or moderately polar water-immiscible solvent such as dichloromethane, diethylether, chloroform, or ethylacetate. Mixtures of these solvents are also suitable. Preferred solvents or solvent mixtures must be determined for each individual case. Specific examples are provided in the experimentals. A suitable solvent can be determined by one of ordinary skill in the art without undue experimentation, as is routinely done in chromatographic methods development (see, e.g., McDonald and Bouvier, eds., Solid Phase Extraction Applications Guide and Bibliography, "A Resource for Sample Preparation Methods Development," 6th edition, Waters, Milford, Mass. (1995); Snyder and Kirkland, Introduction to Modern Liquid Chromatography, New York: J. Wiley and Sons (1974)).

The level of the desorbed solute present in the solvent can be analytically determined by a variety of techniques known to those skilled in the art, e.g., high performance liquid chromatography, liquid chromatography/mass spectrometry, gas chromatography, gas chromatography/mass spectrometry, or immunoassay.

The invention also provides separation devices comprising the porous materials of the invention. Such devices include chromatographic columns, cartridges, thin layer chromatographic plates, filtration membranes, sample clean up devices, solid phase organic synthesis supports, and microtiter plates. In certain embodiments, more than one type of functionalized porous material can be used in the separation devices, e.g., columns, cartridges, and the like.

As noted above, the porous materials of the invention are especially well suited for solid phase extraction. Thus, the invention also includes a solid phase extraction cartridge comprising a porous material of the invention packed inside an open-ended container. In one embodiment, the porous material is packed as particles within the open-ended container to form a solid phase extraction cartridge.

The container can be, e.g., a cylindrical container or column, which is open at both ends so that the solution can enter the container through one end, contact the porous material within the container, and exit the container through the other end.

In the form of porous particles, the porous material can be packed within the container as small particles, such as beads having a diameter between about 3 μm and about 500 μm; between about 5 μm and about 200 μm; or between about 10 μm and about 50 μm. In certain embodiments, the porous particles can be packed in the container enmeshed in a porous membrane.

The container can be formed of any material, which is compatible, within the time frame of the solid phase extraction process, with the solutions and solvents to be used in the procedure. Such materials include glass and various plastics, such as high density polyethylene and polypropylene. In one embodiment, the container is cylindrical through most of its length and has a narrow tip at one end. One example of such a container is a syringe barrel. The amount of porous material within the container is limited by the container volume and can range from about 0.001 g to about 50 kg, and preferably is between about 0.025 g and about 1 g. The amount of porous material suitable for a given extraction depends upon the amount of solute to be sorbed, the available surface area of the porous material and the strength of the interaction between the solute and the porous material. This amount can be readily determined by one of ordinary skill in the art. The cartridge can be a single use cartridge, which is used for the treatment of a single sample and then discarded, or it can be used to treat multiple samples.

EXAMPLES

The present invention may be further illustrated by the following non-limiting examples. All reagents were used as received unless otherwise noted. Those skilled in the art will recognize that equivalents of the following supplies and suppliers exist, and as such the suppliers listed below are not to be construed as limiting.

Materials. All materials were used as received, except as noted. N-vinylcaprolactam and NVP were obtained from ISP, Sodium oleyl sulfate was obtained from ALCOLAC. Diethethylbenzene, 2-ethylhexanol, were obtained from ALDRICH. AIBN was obtained from DUPONT. Methocel E-15 and Divinylbenzene were purchased from DOW. Inhibitor was removed from DVB prior to use.

General. Those skilled in the art will recognize that equivalents of the following instruments and suppliers exist and, as such, the instruments listed below are not to be construed as limiting. The % N values were measured by combustion analysis (CE-440 Elemental Analyzer; Exeter Analytical Inc., North Chelmsford, Mass.). The specific surface areas (SSA) and the average pore diameters (APD) of these materials were measured using the multi-point $N_2$ sorption method (Micromeritics ASAP 2400; Micromeritics Instruments Inc., Norcross, Ga., or equivalent). The specific surface area was calculated using either the BJH method or the BET method, and the average pore diameter was calculated from the desorption leg of the nitrogen isotherm at 77.3K. The BJH SSA was correlated to pore diameter using the nitrogen desorption isotherm from the BJH method.

Median Pore Diameter. The median pore sizes of these materials were determined by inverse size exclusion chromatography (I-SEC). (H. Guan and G. Guiochon, J. of Chromatogr. A, 731 (1996) 27-40). Polystyrene (PS) standards were run with tetrahydrofuran mobile phase. Toluene was used for the determination of the total pore volume (Vt) from the internal pores and external pores. The molecular size in angstrom is calculated by dividing the molecular weight of the PS standard by 41.4. (J. M. Evans, *POLYMER ENGINEERING AND SCIENCE*, Vol. 73 (1973) 401-408). The exclusion volume (Ve) is determined from the intersection of the two linear lines for the external and internal pores in the plot of the logarithm of molecular sizes of PS standards versus their retention volumes. The median pore diameter is defined as the molecular size corresponding to 50% internal pore volume, that is, at the retention volume equal to (Vt+Ve)/2.

Particle Synthesis.

Method 1—Resin Kettle/Inline Static Mixer Syntheses (Small Scale).

Figure 4:
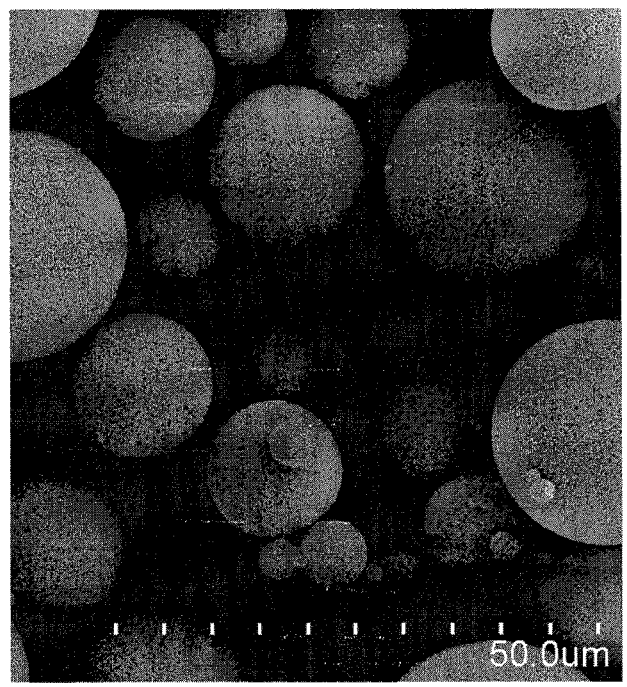
FIG. 4 shows SEM depictions of representative materials of the invention produced during scaled productions and a close-up comparison of the materials of the invention as compared to a standard material produced using toluene and N-vinylpyrrolidone.
Figure 4:
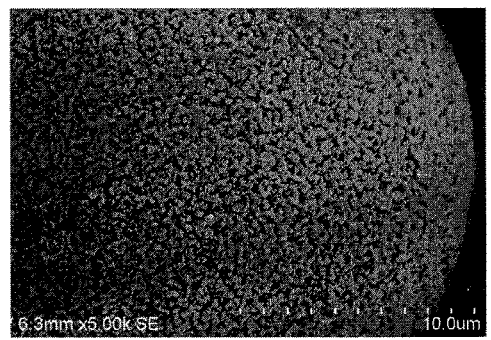
Figure 4:
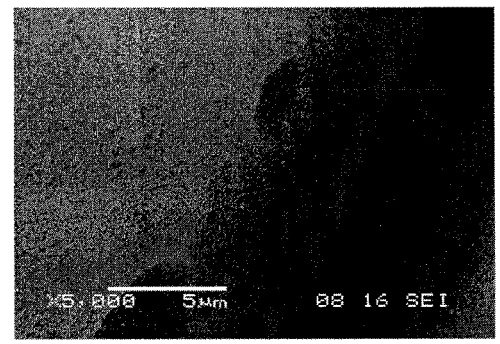

These materials were synthesized in a 3 L kettle with an overhead stirrer, an inline static mixer and a peristaltic pump (FIG. 4). In all cases, the aqueous phase was prepared by dissolving 5.05 g of Methocel in 1 L of water @ 90° C. and allowing the mixture to cool to room temperature. Sodium oleyl sulfate (Sipex OS, ALCOLAC), for reactions requiring it, was added to the aqueous phase when it reached ~50° C. The organic phase was prepared by combining the requisite amounts of DVB and either NVP or V-Cap with 1.9 g of AIBN and the requisite amounts of porogens (toluene, diethylbenzene and/or 2-ethylhexanol) in a 3 L, 4-neck kettle equipped with an overhead stirrer and a Thermowatch apparatus. With the overhead mixer turned on low, the aqueous solution was slowly added. At this point, a peristaltic pump (Cole-Parmer MasterFlex Model 7520-00), equipped with an inline static mixer was attached to the kettle via glass tubes (19/24 joints) connected to the inlet and outlet lines of the pump. The system was then purged with Ar, the overhead mixer was set to 400 RPM, and the peristaltic pump was set to 6 (~900 mL/ min.). After mixing for ~30 minutes, the droplet size and longevity was checked using a light microscope. The target particle size was 10-30 μm in diameter, with droplets lasting for greater than 30 sec. before collapse. If these conditions were met, the peristaltic pump was allowed to empty into the kettle and then shut off. The solution was heated to 70° C., allowed to stir overnight (~16 hours), and then cooled to room temperature. The mixture was poured into a 3 L glass filter equipped with a 20 μm cloth, the mother liquor was filtered, and the particles were washed with 3×600 mL of methanol. The resulting material was dried in a vacuum oven overnight at 80° C. and then submitted for analysis.

Example 1

Material Using N-vinylcaprolactam Having High Percent N/Standard Average Pore Diameter A 5 g amount of Methocel E-15 (Dow Chemical) was dissolved in 1 L of water at 90° C., then cooled to room temperature. In a separate flask, 174.5 g of divinylbenzene (DVB 80, Dow Chemical), 139.2 g of N-vinylcaprolactam (V-Cap, International Specialty Products, Wayne, N.J.), and 1.9 g of azobisisobutyronitrile (AIBN, DuPont) were dissolved and mixed in 243 g of toluene. The organic and aqueous phases were combined in a 3 L glass kettle and stirred at 400 rpm with an overhead stirrer, while running through a static mixing loop for 30 minutes. The emulsion droplet size was checked after 30 minutes. Once the desired droplet size range had been reached (by adjusting the rate of flow through the static mixer), the static mixing loop was turned off; and the mixture heated at 70° C. for 16 hours, then cooled to room temperature. The mixture was filtered using a 20 um polyester filter cloth, washed 3× with 600 mL of methanol and dried for 16 hours under vacuum at 80° C. % N—3.34; SA—562 m$^2$/g, BET AP—88.5 Å.

Example 2

Material Using N-Vinylcaprolactam—Standard percent N/Standard Pore Diameter

A 5g amount of Methocel E-15 (Dow Chemical) was dissolved in 1 L of water at 90 ° C., then cooled to room temperature. In a separate flask, 174.5 g of divinylbenzene (DVB 80, Dow Chemical), 87.1 g of N-vinylcaprolactam (V-Cap, International Specialty Products, Wayne, N.J.), and 1.9 g of azobisisobutyronitrile (AIBN, DuPont) were dissolved and mixed in 243 g of toluene. The organic and aqueous phases were combined in a 3 L glass kettle and stirred at 400 rpm with an overhead stirrer, while running through a static mixing loop for 30 minutes. The emulsion droplet size was checked after 30 minutes. Once the desired droplet size range had been reached (by adjusting the rate of flow through the static mixer), the static mixing loop was turned off, and the mixture heated at 70° C. for 16 hours, then cooled to room temperature. The mixture was filtered using a 20 μm polyester filter cloth, washed 3× with 600 mL of methanol and dried for 16 hours under vacuum at 80° C. % N—1.70; SA—807 m$^2$/g, BET APD—77.0 Å.

Example 3

Material Using Polar Porogens—Standard Percent N/High Pore Diameter

A 5 g amount of Methocel E-15 (Dow Chemical) was dissolved in 1 L of water at 90° C. After cooling to 50° C., 3.24 g of sodium oleyl sulfate (Sipex OS, ALCOLAC) was added, and then the solution was cooled to room temperature. In a separate flask, 174.5 g of divinylbenzene (DVB 80, Dow Chemical), 139.2 g of N-vinylcaprolactam (V-Cap, International Specialty Products, Wayne, N.J.), and 1.9 g of azobisisobutyronitrile (AIBN, DuPont) were dissolved in a mixture of 106 g of diethylbenzene and 128.9 g of 2-ethylhexanol. The organic and aqueous phases were combined in a 3 L glass kettle and stirred at 400 rpm with an overhead stirrer, while running through a static mixing loop for 30 minutes. The emulsion droplet size was checked after 30 minutes. Once the desired droplet size range had been reached (by adjusting the rate of flow through the static mixer), the static mixing loop was turned off, and the mixture heated at 70° C. for 16 hours, then cooled to room temperature. The mixture was filtered using a 20 μm polyester filter cloth, washed 3× with 600 mL of methanol and dried for 16 hours under vacuum at 80° C. % N—2.05; SA—552 m$^2$/g, BET APD—145.9 A Example 4

Material using Polar Porogens and Increased N-Vinylcaprolactam—High Percent N/High Pore Diameter A 5 g amount of Methocel E-15 (Dow Chemical) was dissolved in 1 L of water at 90° C. After cooling to 50° C., 3.24 g of sodium oleyl sulfate (Sipex OS, ALCOLAC) was added, and then the solution was cooled to room temperature. In a separate flask, 174.5 g of divinylbenzene (DVB 80, Dow Chemical), 208.8 g of N-vinylcaprolactam (V-Cap, International Specialty Products, Wayne, N.J.), and 1.9 g of azobisisobutyronitrile (AIBN, DuPont) were dissolved in a mixture of 106 g of diethylbenzene and 128.9 g of 2-ethylhexanol. The organic and aqueous phases were combined in a 3 L glass kettle and stirred at 400 rpm with an overhead stirrer, while running through a static mixing loop for 30 minutes. The emulsion droplet size was checked after 30 minutes. Once the desired droplet size range had been reached (by adjusting the rate of flow through the static mixer), the static mixing loop was turned off, and the mixture heated at 70° C. for 16 hours, then cooled to room temperature. The mixture was filtered using a 20 μm polyester filter cloth, washed 3× with 600 mL of methanol and dried for 16 hours under vacuum at 80° C. % N—2.68; SA—458 m$^2$/g, BET APD—193 Å.

The materials of the invention produced in Examples 1-4 above are summarized in the table below (Table 1)

TABLE 1

Summary of Representative Materials.

| Example # | % N | BET SSA (m$^2$/g) | BET APD (Å) |
|---|---|---|---|
| 1 | 3.34 | 562 | 88.5 |
| 2 | 1.70 | 807 | 77.0 |
| 3 | 2.05 | 552 | 145.9 |
| Repeat of 3 | 2.09 | 576 | 149.1 |
| Repeat of 3 | 2.18 | 528 | 157.5 |
| 4 | 2.68 | 458 | 193 |

Example 5 a)-i) Scaled Production—Varied Percent N/Pore Diameter

A 55 g amount of Methocel E-15 (Dow Chemical) was dissolved in 12 L of water at 90° C. After cooling to 50° C., 35.3 g of sodium oleyl sulfate (Sipex OS, ALCOLAC) was added, and then the solution was cooled to room temperature. In a 5 L RBF, divinylbenzene (DVB 80, Dow Chemical), N-vinylcaprolactam (V-Cap, International Specialty Products, Wayne, N.J.), and 20.7 g of azobisisobutyronitrile (AIBN, DuPont) were dissolved in a mixture of diethylbenzene and 2-ethylhexanol. The organic and aqueous phases were combined in a 33 L glass reactor equipped with baffles, and stirred overhead stirrer at a rate appropriate to achieve an oil droplet size of 20 μm. The emulsion droplet size was checked after 30 minutes. The mixture was then heated at 70° C. for 16 hours, then cooled to room temperature. The mixture was filtered using a 2 μm polyester filter cloth, washed 3× with 600 mL of methanol and dried for 16 hours under vacuum at 80° C. Particles from these syntheses were highly spherical. See Table 2 for amounts and analytical data. See Table 3 for cumulative surface areas associated with various pore diameter ranges and percentages of total SA accounted for by those ranges. See FIG. 4 for representative SEM images. All materials were sized to 20 μm, with a 90/10 (v,v) ratio of 2.

TABLE 2

Reagent Amounts and Analytical Data

| Example 5 | DVB 80 (g) | V-Cap (g) | DEB (g) | 2-EH (g) | % N | BET SSA ($m^2/g$) | BET APD (Å) | MPD (Å from I-SEC)[a] |
|---|---|---|---|---|---|---|---|---|
| a | 1902 | 1517 | 1155 | 1405 | 1.84 | 585 | 166 | / |
| b | 1902 | 1896 | 1155 | 1405 | 2.24 | 566 | 177 | 429 |
| c | 1902 | 1517 | 863 | 1685 | 1.88 | 538 | 190 | / |
| d | 1902 | 1896 | 863 | 1685 | 2.36 | 509 | 368 | 521 |
| e | 1902 | 2655 | 1155 | 1405 | 3.08 | 432 | 214 | 308 |
| f | 1902 | 1517 | 525 | 2008 | 2.01 | 448 | 218 | / |
| g | 1902 | 2655 | 525 | 2008 | 3.12 | 295 | 245 | 303 |
| h | 1902 | 1896 | 525 | 2008 | 2.21 | 439 | 172 | 860 |
| i | 1902 | 2655 | 863 | 1685 | 2.83 | 421 | 199 | 450 |

[a] for comparison, the MPD of a representative material from U.S. Pat. No. 5,882,521 was measured as 74 Å

TABLE 3

BJH Specific Surface Area Calculation

| | Pore Diameter Range (Å) | Material 5 a) | 5 b) | 5 c) | 5 d) | 5 e) | 5 f) | 5 g) | 5 h) | 5 i) | Comp. Material 1[b] |
|---|---|---|---|---|---|---|---|---|---|---|---|
| Cumulative Surface Area of Pores from BJH Desorption Curve ($m^2/g$) | 17-2000 (Total SA) | 376.1 | 356.2 | 324.7 | 149.7 | 261.2 | 238.6 | 169.1 | 237.8 | 253.9 | 537.3 |
| | 300-2000 | 77.7 | 74.3 | 69.8 | 65.7 | 66.2 | 43.8 | 38.8 | 35.1 | 46.8 | 1.6 |
| | 200-2000 | 100.4 | 94.8 | 87.5 | 81.9 | 83.7 | 54.9 | 49.8 | 46.7 | 61.7 | 34.2 |
| % of Specific Surface Area[a] | 300-2000 | 20.7 | 20.9 | 21.5 | 43.9 | 25.4 | 18.3 | 23.0 | 14.8 | 18.4 | 0.3 |
| | 200-2000 | 26.7 | 26.6 | 26.9 | 54.7 | 32.0 | 23.0 | 29.5 | 19.6 | 24.3 | 6.4 |

[a] % of Specific Surface Area calculated by:

$$\left(\frac{\text{Cumulative SA from } x\text{-}2000 \text{ Å}}{\text{Cumulative SA from } 17\text{-}2000 \text{ Å}}\right) * 100$$

where x = 200 or 300

[b] Comparative Material 1 is a representative material from U.S. Pat. No. 5,882,521 having a nominal particle size of 30 μm.

Example 6

Large Scale Run Using Polar Porogens and NVP

Figure 5:
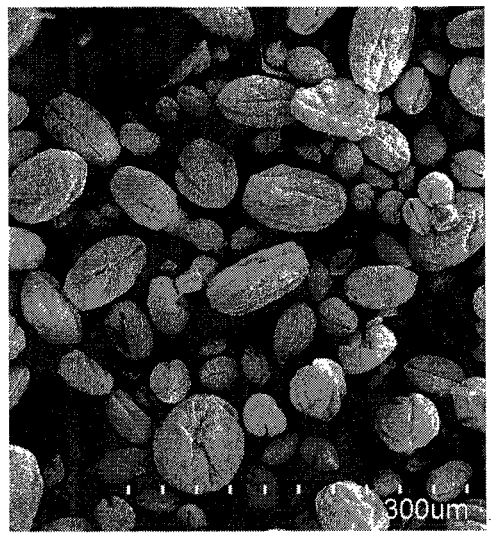
FIG. 5 shows an SEM depiction of a material produced using polar porogens, DVB and N-vinylpyrrolidone which demonstrates the inability of N-vinylpyrrolidone to produce wide pore materials like the materials of the invention.

A 55 g amount of Methocel E-15 (Dow Chemical) was dissolved in 12 L of water at 90° C. In a 5 L RBF, 1902 g of divinylbenzene (DVB 80, Dow Chemical), 1137 g of N-vinylpyrrolidone (NVP, International Specialty Products, Wayne, N.J.), and 20.7 g of azobisisobutyronitrile (AIBN, DuPont) were dissolved in a mixture of diethylbenzene and 2-ethylhexanol. The organic and aqueous phases were combined in a 33 L glass reactor equipped with baffles, and stirred overhead stirrer at a rate appropriate to achieve an oil droplet size of 20 μm. The emulsion droplet size was checked after 30 minutes. Unlike in example 5, the emulsion was unstable, and separated into the respective aqueous and organic components within 5 minutes. The mixture was then heated at 70° C. for 16 hours, then cooled to room temperature. The mixture was filtered using a 2 μm polyester filter cloth, washed 3× with 600 mL of methanol and dried for 16 hours under vacuum at 80° C. Material obtained from this synthesis has a failed morphology—it was irregular in shape and size. SEM images (FIG. 5) indicate particle collapse. % N=1.5

Example 7

Synthesis of a Wide Pore Weak Anion Exchanger

A 20 g sample of material 5 d) was converted to a weak anion exchanger following the procedure given in U.S. Pat. No. 7,731,844 (Ion exchange capacity=0.387 meq/g)

Example 8

Use of Wide Pore Material Weak Anion Exchanger for the Purification of Oligonucleotides in Plasma A series of polythymidine oligonucleotides were analyzed for recovery (Table 4) from plasma on material 7 and Comparative Material 2 (2 mg per well in μelution plates—Comparative Material 2 is a representative material from U.S. Pat. No. 7,731,884 having a nominal particle size of 30 μm), according to the following protocol:

a) Condition with 200 μL methanol
b) Equilibrate 200 μL 100mM $NaH_2PO_4$ 2 mM $NaN_3$ in water, pH 5.5
c) Dilute stock oligonucleotide 10:1 with plasma, then:
   i) Dilute plasma/oligomer standard 1:1 with citrate buffer/ 2 mM $NaN_3$ solution (200mM citrate 2 mM $NaN_3$ in water, pH 5.5)
   or
   ii) Dilute plasma oligomer/standard to make a 10% acetonitrile, 45% plasma/oligomer standard, 45% $NaH_2PO_4$/2 mM $NaN_3$ solution (100 mM $NaH_2PO_4$ 2 mM $NaN_3$ in water, pH 5.5)
d) Load 100 μL of oligo plasma sample (0.4 nmole/mL)
e) Wash 100 μL 1% HCOOH
f) Wash with 100 μL 60% methanol
g) Elute 50 μL*2 30% methanol /70% 30 mM triethylamine in water
h) Elute 100 μL 30% methanol/70% 30 mM triethylamine in water
i) Measure recovery by comparison to standard using a photodiode array.

TABLE 4

Comparison of oligonucleotide recoveries from plasma for different materials

| Polythymidine Oligomer | Plasma Dilution Step Utilized | Material Utilized | % Recovery |
|---|---|---|---|
| 15mer | c i) | Example 7 | 91 |
| | | Comp. Material 2 | 50 |
| | c ii) | Example 7 | 98 |
| | | Comp. Material 2 | 63 |
| 20mer | c i) | Example 7 | 91 |
| | | Comp. Material 2 | 45 |
| | c ii) | Example 7 | 94 |
| | | Comp. Material 2 | 39 |
| 25mer | c i) | Example 7 | 88 |
| | | Comp. Material 2 | 33 |
| | c ii) | Example 7 | 71 |
| | | Comp. Material 2 | 13 |
| 30mer | c i) | Example 7 | 84 |
| | | Comp. Material 2 | 20 |
| | c ii) | Example 7 | 65 |
| | | Comp. Material 2 | 6 |
| 35mer | c i) | Example 7 | 72 |
| | | Comp. Material 2 | 11 |
| | c ii) | Example 7 | 69 |
| | | Comp. Material 2 | 5 |

Example 9

Use of Wide Pore Material for the Purification of Proteins a) A test mixture of several proteins was analyzed for recovery (Table 5) on material 5 g), Comparative Material 1 and Comparative Material 3 (2 mg per well in μelution plates) (Comparative Material 1 is described above; Comparative Material 3 is a representative material from U.S. Pat. No. 5,882,521 having a nominal particle size of 20 μm) and according to the following protocol:
1) Condition plate with 200 μL methanol
2) Condition plate with 200 μL water
3) Load 100 μL diluted protein standard (2.5% ACN and 0.05% TFA in water)
4) Wash with 200 μL 5% methanol in water
5) Elute with 2× 25 μL of 3:1 methanol/water with 1% trifluoroethanol
6) Dilute with protein solution for blank and 2.5% acetonitrile and 0.05% TFA in water for sample.
7) Measure recovery by HPLC/UV

TABLE 5

Comparison of protein recoveries for different materials using protocol a)

| Peptide | Size (Approx. MW) | [Protein] (mg/mL) | Material Utilized | % Recovery |
|---|---|---|---|---|
| Insulin | 5734 | 10 | Example 5 g) | 90 |
| | | | Comp. Material 3 | 61 |
| | | | Comp. Material 1 | 30 |
| Cytochrome C | 12384 | 4 | Example 5 g) | 39 |
| | | | Comp. Material 3 | 2 |
| | | | Comp. Material 1 | 8 |
| Ribonuclease A | 13700 | 4 | Example 5 g) | 56 |
| | | | Comp. Material 3 | 0 |
| | | | Comp. Material 1 | 0 |
| Myoglobin | 16951 | 10 | Example 5 g) | 20 |
| | | | Comp. Material 3 | 2 |
| | | | Comp. Material 1 | 2 | b) A test mixture of several proteins was analyzed for recovery (Table 6) on material 5 g), Comparative Materials 1 and 3 (2 mg per well in μelution plates, according to the following protocol:
1) Condition plate with 200 μL methanol
2) Condition plate with 200 μL water
3) Load 100 μL diluted protein standard
4) Wash with 200 μL 5% methanol in water
5) Elute with 2×25 μL of 3:1 acetonitrile/water with 5% trifluoroacetic acid
6) Dilute with protein solution for blank and 2.5% acetonitrile and 0.05% TFA in water for sample.
7) Measure recovery by HPLC/UV

TABLE 6

Comparison of protein recoveries for different materials utilizing protocol b)

| Peptide | Size (Approx. MW) | [Protein Standard] (mg/mL) | Material Utilized | % Recovery |
|---|---|---|---|---|
| Insulin | 5734 | 10 | Example 5 g) | 100 |
| | | | Comp. Material 3 | 85 |
| Cytochrome C | 12384 | 4 | Example 5 g) | 93 |
| | | | Comp. Material 3 | 61 |
| Ribonuclease A | 13700 | 4 | Example 5 g) | 65 |
| | | | Comp. Material 3 | 0 |
| Myoglobin | 16951 | 10 | Example 5 g) | 62 |
| | | | Comp. Material 3 | 2 |
| β-lactoglobulin | 18270 | 4 | Example 5 g) | 25 |
| | | | Comp. Material 3 | 1 |
| Apo-Transferrin | 78000 | 10 | Example 5 g) | 42 |
| | | | Comp. Material 3 | 0 |

Example 10

Monolith Synthesis

The aqueous and organic solutions are prepared as in Example 5, except that no sodium oleyl sulfate is added to the aqueous phase. Following purging of each of the solutions for 10 minutes with Ar, the organic and aqueous phases are combined in small glass vials in the same ratio as in Example 5. Each of the vials is then sealed with a stopper, placed vertically in a thermostated oil bath, heated at 70° C. for 16 hours, and cooled to room temperature.

Incorporation By Reference

The entire contents of all patents, published patent applications and other references cited herein are hereby expressly incorporated herein in their entireties by reference.

Equivalents

Those skilled in the art will recognize, or be able to ascertain using no more than routine experimentation, numerous equivalents to the specific procedures described herein. Such equivalents were considered to be within the scope of this invention and are covered by the following claims.

What is claimed is:

1. A porous material comprising a random copolymer of a least one hydrophobic monomer and at least one hydrophilic monomer, wherein more than 10% of the BJH surface area of the porous material is contributed by pores that have a diameter greater than or equal to 200 Å, wherein said hydrophilic monomer is N-vinylcaprolactam and wherein said hydrophobic monomer is divinylbenzene; and wherein the porous material comprises porous particles that comprises said random copolymer;

and wherein the nitrogen content of said material is from about 1% N to about 4% N;

and wherein all of the particles of the material are spherical.

2. The porous material of claim 1, wherein the BJH surface area of the porous material is determined from a nitrogen desorption isotherm at 77.3K.

3. The porous material of claim 1, wherein more than 10% of the BJH surface area of the porous material is contributed by pores that have a diameter greater than or equal to 300 Å.

4. The porous material of claim 1, wherein said material has a median pore diameter of about 100 Å to about 1000 Å.

5. The porous material of claim 4, wherein said material has a median pore diameter of about 300 Å.

6. The porous material of claim 1 wherein said copolymer is a poly(divinylbenzene-co-N-vinylcaprolactam).

7. The porous material of claim 6 wherein the poly(divinylbenzene-co-N-vinylcaprolactam) has ion-exchange functional moieties present at a concentration of about 0.01 to about 10.0 milliequivalents per gram of porous material.

8. A porous material comprising a random copolymer of at least one hydrophobic monomer and at least one hydrophilic monomer, wherein said material has a median pore diameter of about 100 Å to about 1000 Å; wherein said hydrophilic monomer is N-vinylcaprolactam and wherein said hydrophobic monomer is divinylbenzene; and wherein the porous material comprises porous particles that comprises said random copolymer;

and wherein the nitrogen content of said material is from about 1% N to about 4% N;

and wherein all of the particles of the material are spherical.

9. The porous material of claim 8, wherein said material has a median pore diameter of about 300 Å to about 800 Å.

10. The porous material of claim 9, wherein said material has a median pore diameter of about 300 Å to about 550 Å.

11. The porous material of claim 10, wherein said material has a median pore diameter of about 300 Å.

12. The porous material of claim 8, wherein said copolymer is a poly(divinylbenzene-co-N-vinylcaprolactam).

13. The porous material of claim 12 wherein the poly(divinylbenzene-co-N-vinylcaprolactam) has ion-exchange functional moieties present at a concentration of about 0.01 to about 10.0 milliequivalents per gram of porous material.

14. A porous material for solid phase extraction or chromatography comprising at least one porous material of claim 1.

15. A porous material for solid phase extraction or chromatography comprising at least one porous material of claim 8.

16. A method for removing or isolating a component from a mixture comprising:

contacting the mixture with a chromatographic material comprising the porous material according to claim 1, to thereby remove or isolate the component from the mixture.

17. The method for removing or isolating a component from a mixture of claim 16, wherein the porous material is a poly(divinylbenzene-co-N-vinylcaprolactam) copolymer.

18. A method for removing or isolating a component from a mixture comprising:

contacting the mixture with a chromatographic material comprising the porous material according to claim 8, to thereby remove or isolate the component from the mixture.

19. The method for removing or isolating a component from a mixture of claim 18, wherein the porous material is a poly(divinylbenzene-co-N-vinylcaprolactam) copolymer.

20. A method for determining the level of a component in a mixture, comprising:

a.) contacting the mixture with a chromatographic material comprising the porous material according to claim 1 under conditions that allow for sorption of the component onto the porous materials;

b.) washing the chromatographic material having the sorbed component with a solvent under conditions so as to desorb the component from the porous materials; and c.) determining the level of the desorbed component.

21. The method for determining the level of a component in a mixture of claim 20, wherein the porous material is a poly(divinylbenzene-co-N-vinylcaprolactam) copolymer.

22. A method for determining the level of a component in a mixture, comprising:

a.) contacting the mixture with a chromatographic material comprising the porous material according to claim 8 under conditions that allow for sorption of the component onto the porous materials;

b.) washing the chromatographic material having the sorbed component with a solvent under conditions so as to desorb the component from the porous materials; and c.) determining the level of the desorbed component.

23. The method for determining the level of a component in a mixture of claim 22, wherein the porous material is a poly(divinylbenzene-co-N-vinylcaprolactam) copolymer.

24. A separation device comprising the porous material according to claim 1.

25. The separation device of claim 24, wherein said device is selected from the group consisting of chromatographic columns, cartridges, thin layer chromatographic plates, filtration membranes, sample clean up devices, solid phase organic synthesis supports, and microtiter plates.

26. A separation device comprising the porous material according to claim 8.

27. The separation device of claim 26, wherein said device is selected from the group consisting of chromatographic columns, cartridges, thin layer chromatographic plates, filtration membranes, sample clean up devices, solid phase organic synthesis supports, and microtiter plates.

28. A solid phase extraction cartridge comprising the porous material according to claim 1.

29. The solid phase extraction cartridge of claim 28, wherein the cartridge comprises an open-ended column that contains the porous material.

30. A solid phase extraction cartridge comprising the porous material according to claim 8.

31. The solid phase extraction cartridge of claim 30, wherein the cartridge comprises an open-ended column that contains the porous material.

* * * * *